(12) United States Patent
Giroud

(10) Patent No.: US 7,357,921 B2
(45) Date of Patent: Apr. 15, 2008

(54) ELECTROPHILIC MONOMERS FOR TREATING THE HAIR

(75) Inventor: Franck Giroud, Clichy (FR)

(73) Assignee: L'Oreal, Paris (FR)

(*) Notice: Subject to any disclaimer, the term of this patent is extended or adjusted under 35 U.S.C. 154(b) by 595 days.

(21) Appl. No.: 10/323,991

(22) Filed: Dec. 18, 2002

(65) Prior Publication Data

US 2003/0175229 A1     Sep. 18, 2003

(51) Int. Cl.
*A61Q 5/00*     (2006.01)

(52) U.S. Cl. .......................... 424/70.11; 424/45; 424/47

(58) Field of Classification Search ...................... None
See application file for complete search history.

(56) References Cited

U.S. PATENT DOCUMENTS

| | | | | |
|---|---|---|---|---|
| 3,634,022 A | | 1/1972 | Robbins et al. ............ 8/127.51 |
| 3,929,403 A | * | 12/1975 | Kalopissis et al. ............. 8/416 |
| 4,049,665 A | * | 9/1977 | Douglass .................... 546/294 |
| 4,128,631 A | * | 12/1978 | Lundmark et al. ........ 424/70.17 |
| 5,082,010 A | * | 1/1992 | Skaryd et al. ............... 132/201 |
| 5,362,486 A | * | 11/1994 | Nandagiri et al. ........ 424/70.11 |
| 5,767,152 A | * | 6/1998 | Nielsen et al. .............. 514/526 |
| 5,804,166 A | * | 9/1998 | Chan et al. .................... 424/47 |
| 6,358,496 B1 | * | 3/2002 | Zink et al. ..................... 424/59 |
| 6,488,922 B1 | * | 12/2002 | Damm et al. .............. 424/70.1 |

FOREIGN PATENT DOCUMENTS

FR     2780280     12/1999

OTHER PUBLICATIONS

Böllert et al., "Polymerisation von quaternisiertem 4-Vinylpyridin auf Humanhaar," Proceedings-Internationale Wolltextil-Forschungskonferenz, 5$^{th}$ 3:403-415, 1976.

* cited by examiner

*Primary Examiner*—Michael P. Woodward
*Assistant Examiner*—Eric E. Silverman
(74) *Attorney, Agent, or Firm*—Fulbright & Jaworski L.L.P.

(57) ABSTRACT

The present invention relates to the use, for treating the hair, of a composition containing, in a cosmetically acceptable medium, at least one monomer capable of polymerizing by anionic polymerization in the presence of a nucleophilic agent.

27 Claims, No Drawings

ELECTROPHILIC MONOMERS FOR TREATING THE HAIR

BACKGROUND OF THE INVENTION

1. Field of the Invention

The present invention relates to the use, for treating the hair, of compositions based on monomers that may be polymerized in situ, and also to the corresponding cosmetic treatment process.

2. Description of Related Art

Cosmetic compositions based on silicones or polymers with high affinity for the hair are generally used, in order to modify the surface properties of the hair, especially to condition it.

It is generally necessary to renew these treatments since conditioners have a tendency to be removed, especially on shampooing.

It is theoretically possible to increase the remanence of the polymer deposit by directly performing a free-radical polymerization of certain monomers on the hair.

However, the treatments thus obtained are cosmetically unacceptable. Considerable degradation of the fiber is generally observed, probably associated with the polymerization initiators, and the treated hair is difficult to disentangle.

SUMMARY OF THE INVENTION

The Applicant has just discovered that it is possible to obtain improved and long-lasting conditioning of the surface of the hair by using electrophilic monomers for which an anionic polymerization process is initiated in the presence of a nucleophilic agent such as hydroxide ions ($OH^-$) contained in water at neutral pH.

The Applicant has more particularly found that by applying a composition based on such monomers to the hair, a polymer is formed in situ. Without wishing this explanation to be limiting, it appears that it is the hydroxide ions contained in the water absorbed by the hair that trigger the anionic polymerization process at the treating composition/hair interface. The polymer thus formed in situ by interfacial anionic polymerization is in the form of a uniform deposit and has excellent adhesion to the hair.

Moreover, it has been found, surprisingly, that the hairs remain perfectly individualized and may be styled without any problems, and that the conditioning of the surface of the fiber is remanent with respect to shampooing.

A first subject of the invention is thus the use of compositions comprising at least one monomer capable of undergoing anionic polymerization in the presence of a nucleophilic agent for treating the hair.

A second subject of the invention is also a process using a composition used in the context of this treatment.

Other subjects of the invention will become apparent on reading the description and the examples that follow.

The expression "anionic polymerization" means the mechanism defined in the book "Advanced Organic Chemistry", Third Edition, by Jerry March, pages 151 to 161.

The monomers used more particularly in accordance with the invention are monomers of structure:

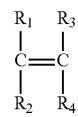

(A)

in which:

$R_1$ and $R_2$ denote, independently of each other, groups with little or no electron-withdrawing nature, such as:

a hydrogen atom, a saturated or unsaturated, linear, branched or cyclic hydrocarbon-based radical, preferably containing from 4 to 20 carbon atoms and possibly containing one or more nitrogen, oxygen or sulphur atoms, and possibly being optionally substituted with one or more groups chosen from OR, COOR, COR, SH, SR and OH, an organomodified or non-organomodified polysiloxane residue, a polyoxyalkylene group, OR, COOR, COR, SH, SR and OH.

$R_3$ and $R_4$ denote, independently of each other, electron-withdrawing groups preferably chosen from $N(R)_{3+}$, $S(R)_{2+}$, $SH_{2+}$, $NH_{3+}$, $NO_2$, $SO_2R$, $C\equiv N$, COOH, F, Cl, Br, I, OR, COOR, COR, SH, SR and OH, linear or branched alkenyl radicals, linear or branched alkynyl radicals and mono- or polyfluoroalkyl groups, R denoting a $C_1$-$C_{10}$ alkyl or $C_1$-$C_{10}$ mono- or polyfluoroalkyl radical and the alkyl groups contain from 1 to 10 carbon atoms. The alkenyl or alkynyl groups preferably contain from 2 to 10 carbon atoms.

Among the organomodified polysiloxanes that may be mentioned are polydimethylsiloxanes containing $C_2$-$C_{30}$ alkyl and/or phenyl and/or siloxy and/or silanol and/or amine and/or imine and/or fluoroalkyl functions.

Among the mono- or polyfluoroalkyl groups that may be mentioned are groups such as $(CH_2)_n$—$(CF_2)_m$—$CF_3$ or $(CH_2)_n$—$(CF_2)_m$—$CHF_2$, with n=1 to 20 and m=1 to 20.

Among the polyoxyalkylene groups that may be mentioned are polyoxyethylene groups and polyoxypropylene groups preferably containing 1 to 200 oxyalkylenated units.

The substituents $R_1$ to $R_4$ may optionally be substituted with a group that has cosmetic activity. The cosmetic activities that are particularly used are colouring, antioxidant, UV-screening and conditioning functions.

Among the monomers mentioned above that are preferred are the monomers of the cyanoacrylate family and the derivatives thereof of formula (B):

(B)

$R_1$ and $R_2$ having the same meanings as above, $R'_3$ possibly denoting a non-electron-withdrawing or electron-withdrawing group such as those defined for formula (A).

Compounds of formula (B) that may be mentioned include monomers consisting of the fluoroalkyl-2-cyanoacrylate family, such as:

a)

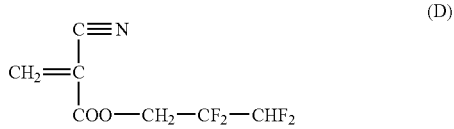

(D)

2,2,3,3-tetrafluoropropyl 2-cyano-2-propenoate, or alternatively:

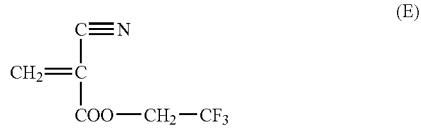

(E)

2,2,2-trifluoroethyl 2-cyano-2-propenoate, or b) ($C_1$-$C_{10}$) alkyl or alkoxy cyanoacrylates and derivatives thereof.

Mention may be made more particularly of: ethyl 2-cyanoacrylate, methyl 2-cyanoacrylate, n-propyl 2-cyanoacrylate, isopropyl 2-cyanoacrylate, tert-butyl 2-cyanoacrylate, n-butyl 2-cyanoacrylate, isobutyl 2-cyanoacrylate, 3-methoxybutyl cyanoacrylate, n-decyl cyanoacrylate, hexyl 2-cyanoacrylate, 2-ethoxyethyl 2-cyanoacrylate, 2-methoxyethyl 2-cyanoacrylate, 2-octyl 2-cyanoacrylate, 2-propoxyethyl 2-cyanoacrylate, n-octyl 2-cyanoacrylate and isoamyl cyanoacrylate.

In the context of the invention, it is preferred to use the monomers b).

The monomer that is most particularly preferred is n-octyl 2-cyanoacrylate:

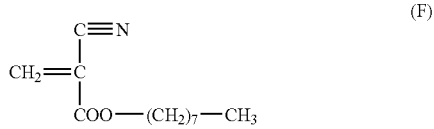

(F)

The monomers used in accordance with the invention may be covalently attached to supports such as polymers, oligomers or dendrimers. The polymer or oligomer may be linear, branched, in comb form or in block form. The distribution of the monomers of the invention over the polymer, oligomer or dendritic structure may be random, in an end position or in the form of blocks.

The nucleophilic agents capable of initiating the anionic polymerization are systems that are known per se, capable of generating a carbanion on contact with a nucleophilic agent, such as the hydroxide ions contained in water at neutral pH. The term "carbanion" means the chemical species defined in "Advanced Organic Chemistry, Third Edition", by Jerry March, page 141.

The nucleophilic agents may consist of a molecular compound, an oligomer, a dendrimer or a polymer containing nucleophilic functions. Nucleophilic functions that may be mentioned, in a non-limiting manner, include the following functions: $R_2N^-$, $NH_2^-$, $Ph_3C^-$, $R_3C^-$, $PhNH^-$, pyridine, $ArS^-$, $R-C\equiv C^-$, $RS^-$, $SH^-$, $RO^-$, $R_2NH$, $ArO^-$, $N_3^-$, $OH^-$, $ArNH_2$, $NH_3$, $I^-$, $Br^-$, $Cl^-$, $RCOO^-$, $SCN^-$, $ROH$, $RSH$, $NCO^-$, $CN^-$, $NO_3^-$, $ClO_4^-$, $H_2O$, etc.

An anhydrous and non-hygroscopic medium is preferably used to convey the monomers of the invention, which may be used in pure form or in the form of an emulsion or may be encapsulated. The expression "anhydrous medium" means a medium containing less than 1% water.

The cosmetically acceptable medium containing the abovementioned monomers is preferably chosen from organic oils, silicones, mineral oils, waxes or organic solvents such as $C_5$-$C_{10}$ alkanes, acetone, methyl ethyl ketone, methyl acetate, butyl acetate, ethyl acetate, dimethoxyethane, diethoxyethane, fatty alcohols, fatty acids, fatty esters, fatty amides and fatty alkyl-benzoates, and mixtures thereof.

The compositions used in accordance with the invention generally have a monomer concentration according to the invention of between 0.001% and 50% by weight and more particularly between 0.1% and 10% by weight.

Polymerization inhibitors, and more particularly free-radical and/or anionic polymerization inhibitors, may also be introduced into the compositions, in order to increase the stability of the composition over time. The following polymerization inhibitors may be mentioned, in a non-limiting manner: sulphur dioxide, nitric oxide, organic acids such as sulphonic acid or phosphoric acid, lactone, boron trifluoride, hydroquinone and its derivatives such as hydroquinone monoethyl ether, TBHQ, benzoquinone and its derivatives such as duroquinone, catechol and its derivatives such as t-butylcatechol and methoxycatechol, anisole and its derivatives such as methoxyanisole or hydroxyanisole, pyrogallol and its derivatives, p-methoxyphenol, hydroxybutyltoluene, alkyl sulphates, alkyl sulphites, alkyl sulphones, alkyl sulphoxides, alkyl sulphides, mercaptans and 3-sulphonene and mixtures thereof. The alkyl groups preferably denote groups containing 1 to 6 carbon atoms.

The concentration of inhibitor in the composition of the invention may be between 10 ppm and 5% and more preferably between 10 ppm and 0.5%, by weight.

The compositions in accordance with the invention may also contain a propellant, which may consist of compressed or liquefied gases usually used for preparing aerosol compositions. Air, carbon dioxide, compressed nitrogen or a soluble gas such as dimethyl ether, halohydrocarbons such as fluoro hydrocarbons or non-fluoro hydrocarbons, and mixtures thereof, will preferably be used.

The compositions in accordance with the invention may also contain agents usually used in cosmetics, such as reducing agents, fatty substances, plasticizers, softeners, antifoams, moisturizers, pigments, clays, mineral fillers, UV screening agents, mineral colloids, peptizers, solubilizing agents, fragrances, preserving agents, anionic, cationic, nonionic or amphoteric surfactants, fixing or non-fixing polymers, polyols, proteins, vitamins, direct dyes or oxidation dyes, nacreous agents, etc.

The hair treatment process in accordance with the invention consists in applying the composition described above to the hair, and in particular in the presence of a nucleophilic agent.

Preferably, this nucleophilic agent is water. This water may be provided by moistening beforehand.

In order to modify the reaction kinetics, it is also possible to moisten the fiber beforehand using an aqueous solution whose pH has been adjusted with the aid of a base, an acid or an acid/base mixture. The acid and/or the base may be mineral or organic.

It is also possible to modify the anionic polymerization kinetics by pre-impregnating the fiber using a nucleophilic agent. The nucleophilic agent may be used in pure form, as a solution or in the form of an emulsion, or may be encapsulated.

To modify the anionic polymerization kinetics, the nucleophilicity of the fiber may also be increased by chemical conversion of the keratin material. Examples that may be mentioned include the reduction of the disulphide bridges, of which keratin is partially composed, into thiols before applying the composition of the invention. In a non-exhaustive manner, agents for reducing the disulphide bridges of which keratin is partially composed that may be mentioned include the following compounds:

anhydrous sodium thiosulphate,
powdered sodium metabisulphite,
thiourea,
ammonium sulphite,
thioglycolic acid,
thiolactic acid,
ammonium thiolactate,
glyceryl monothioglycolate,
ammonium thioglycolate,
thioglycerol,
2,5-dihydroxybenzoic acid,
diammonium dithioglycolate,
strontium thioglycolate,
calcium thioglycolate,
zinc formaldehydesulphoxylate,
isooctyl thioglycolate,
d,l-cysteine,
monoethanolamine thioglycolate.

To modify the anionic polymerization kinetics, and more specifically to reduce the rate of polymerization of the monomers of the invention, it is possible to increase the viscosity of the composition. To do this, one or more polymers having no reactivity towards the monomers in accordance with the invention may be added to the composition of the invention. In this context, mention may be made, in a non-exhaustive manner, of polymethyl methacrylate (PMMA) or copolymers based on cyanoacrylate such as those described in U.S. Pat. No. 6,224,622.

In order to improve, inter alia, the adhesion of the poly(cyanoacrylate) formed in situ, the fiber may be pre-treated with polymers of any type, or a hair treatment may be performed before applying the composition of the invention, for instance a direct dyeing or oxidation dyeing operation, a permanent-waving operation or a hair-straightening operation.

The application of the compositions in accordance with the invention may optionally be followed by rinsing. These compositions may be in various forms, such as in the form of a lotion, spray or a mousse and may be applied in the form of a shampoo or a conditioner.

DETAILED DESCRIPTION OF THE ILLUSTRATIVE EMBODIMENTS

The examples that follow are intended to illustrate the invention without being limiting in nature.

EXAMPLE 1

The following composition was prepared:

| | |
|---|---|
| n-Octyl 2-cyanoacrylate (1) | 10 g |
| Silicone oil (2) | 90 g |

RITE LOK CON895, sold by the company Chemence
Dow Corning 556 Fluid Cosmetic

Application Method 1

2 g of composition described above are applied to a lock consisting of 2.7 g of sensitized hair with an alkaline solubility equal to 20%. After leaving the composition in contact with the lock of hair for one minute, the lock is washed using a DOP camomile shampoo and then dried for 1 hour at room temperature.

The same operation is also performed on another lock with the silicone oil alone.

Application Method 2

A lock consisting of 2.7 g of sensitized hair with an alkaline solubility equal to 20% is moistened with 1 ml of water. 2 g of composition described above are applied to this moistened lock. After leaving the composition in contact with the lock of hair for one minute, the lock is washed using a DOP camomile shampoo and then dried for 1 hour at room temperature.

The same operation is also performed on another lock moistened with the silicone oil alone.

For each lock, the feel of the hair is evaluated by a panel of 10 individuals. An untreated lock of the same alkaline solubility is used as reference.

The tactile evaluation of the various locks of hair is repeated with the same procedure after having washed them 5 times successively using the shampoo sold under the name DOP camomile.

Results

| | Nature of the treatment | Application method 1 | | Application method 2 | |
|---|---|---|---|---|---|
| | | Composition | Silicone | Composition | Silicone |
| Feel of the fiber | After application + shampooing | Coated 3 Greasy 4 | Coated 0 Greasy 5 | Coated 4 Greasy 3 | Coated 0 Greasy 4 |
| | After shampooing 5 times | Coated 3 Greasy 0 | Coated 0 Greasy 0 | Coated 3 Greasy 0 | Coated 0 Greasy 0 |

Grading: 0 undetectable → 5 very pronounced

The experiment shows that the change in the feel of the fiber provided by the monomer according to the invention (coated feel) is remanent with respect to shampooing, whereas the change in the feel provided by the silicone (greasy feel) is not remanent with respect to shampooing. The composition thus makes it possible to conserve, after shampooing several times, the modified feel, and does so without reapplying the composition.

The invention claimed is:

1. A method for conditioning the surface of the hair comprising:
    obtaining a composition comprising at least one monomer capable of polymerizing by anionic polymerization in the presence of a nucleophilic agent in a cosmetically acceptable medium; and
    applying the composition to the surface of the hair in the presence of a nucleophilic agent capable of initiating the anionic polymerization;
    wherein the at least one monomer is a monomer of formula:

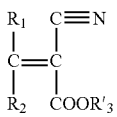

wherein:
R₁ and R₂ denote, independently of each other:
a hydrogen atom;
a saturated or unsaturated, linear or branched hydrocarbon-based radical comprising from 4 to 20 carbon atoms; polysiloxane residue;
a polyoxyalkylene group; or
OR, COOR, COR, SH, SR and OH;
wherein any R denotes a C1-C10 alkyl or C1-C10 mono- or polyfluoroalkyl radical; and
R'₃ is a non-electron-withdrawing or electron-withdrawing group, further defined as:
a hydrogen atom
a saturated or unsaturated, linear, branched or cyclic hydrocarbon-based radical containing from 4 to 20 carbon atoms;
a polysiloxane residue:
a polyoxyalkylene group; or
a linear or branched alkenyl radical, linear or branched alkynyl radical, or mono- or polyfluoroalkyl group containing 2 to 10 carbon atoms;
and wherein the at least one monomer forms part or all of a total monomer concentration of between 0.1% and 10% by weight.

2. The method of claim 1, wherein at least one of R₁ and R₂ denotes a saturated or unsaturated, linear or branched hydrocarbon-based radical comprising from 4 to 20 carbon atoms.

3. The method of claim 2, wherein the saturated or unsaturated, linear or branched hydrocarbon-based radical comprises one or more nitrogen, oxygen or sulphur atoms.

4. The method of claim 2, wherein the saturated or unsaturated, linear or branched hydrocarbon-based radical is substituted with one or more group, the group further defined as OR, COOR, COR, SH, SR and/or OH, wherein any R denotes a $C_1$-$C_{10}$ alkyl or $C_1$-$C_{10}$ mono- or polyfluoroalkyl radical.

5. The method of claim 1, wherein the at least one monomer is a ($C_1$-$C_{10}$) alkyl or alkoxy cyanoacrylate.

6. The method of claim 5, wherein the at least one monomer is ethyl 2-cyanoacrylate, methyl 2-cyanoacrylate, n-propyl 2-cyanoacrylate, isopropyl 2-cyanoacrylate, tert-butyl 2-cyanoacrylate, n-butyl 2-cyanoacrylate, isobutyl 2-cyanoacrylate, 3-methoxybutyl cyanoacrylate, n-decyl cyanoacrylate, hexyl 2-cyanoacrylate, 2-ethoxyethyl 2-cyanoacrylate, 2-methoxyethyl 2-cyanoacrylate, 2-octyl 2-cyanoacrylate, 2-propoxyethyl2-cyanoacrylate, n-octyl 2-cyanoacrylate, or isoamyl cyanoacrylate.

7. The method of claim 6, wherein the at least one monomer is n-octyl 2-cyanoacrylate.

8. The method of claim 1, wherein the medium is further defined as an anhydrous and non-hygroscopic medium.

9. The method of claim 8, wherein the medium comprises an organic oil, silicone, mineral oil, wax, or organic solvent.

10. The method of claim 9, wherein the medium comprises an organic solvent further defined as a $C_5$-$C_{10}$ alkane, acetone, methyl ethyl ketone, methyl acetate, butyl acetate, ethyl acetate, dimethoxyethane, diethoxyethane, fatty alcohol, fatty acid, fatty ester, fatty amide, or fatty alkylbenzoate.

11. The method of claim 1, wherein the composition contains at least one polymerization inhibitor.

12. The method of claim 11, wherein the at least one polymerization inhibitor is a free-radical and/or anionic polymerization inhibitor.

13. The method of claim 12, wherein the at least one polymerization inhibitor is further defined as comprising sulphur dioxide, nitric oxide, an organic acid, lactone, boron trifluoride, hydroquinone, a hydroquinone monoethyl ether, TBHQ, benzoquinone, a duroquinone, catechol, t-butylcatechol, methoxycatechol, anisole, methoxyanisole, hydroxyanisole, pyrogallol, p-methoxyphenol, hydroxybutyltoluene, an alkyl sulphate, an alkyl sulphite, an alkyl sulphone, an alkyl sulphoxide, an alkyl sulphide, a mercaptan, or a 3-sulphonene.

14. The method of claim 13, wherein the at least one polymerization inhibitor is an organic acid further defined as sulphonic acid or phosphoric acid.

15. The method of claim 11, wherein the polymerization inhibitor is present in a concentration of between 10 ppm and 5%.

16. The method of claim 15, wherein the polymerization inhibitor is present in a concentration of between 10 ppm and 0.5% by weight.

17. The method of claim 1, wherein the composition further comprises at least one reducing agent, fatty substance, plasticizer, softener, antifoam, moisturizer, pigment, clay, mineral filler, UV screening agent, mineral colloid, peptizer, solubilizing agent, fragrance, preserving agent, anionic surfactant, cationic surfactant, nonionic surfactant, amphoteric surfactant, fixing polymer, non-fixing polymer, polyol, protein, vitamins, direct dye, oxidation dye, or nacreous agent.

18. The method of claim 17, wherein the composition is in the form of a lotion, a spray or a mousse.

19. The method of claim 1, wherein the composition contains a propellant.

20. The method of claim 19, wherein the propellant comprises a compressed or liquefied gas.

21. The method of claim 1, wherein the nucleophilic agent is a molecular compound, an oligomer, a dendrimer, or a polymer containing nucleophilic functions chosen from: $R_2N^-$, $NH_2^-$, $Ph_3C^-$, $R_3C^-$, $PhNH^-$, pyridine, $ArS^-$, $R—C\equiv C^-$, $RS^-$, $SH^-$, $RO^-$, $R_2NH$, $ArO^-$, $N_3^-$, $OH^-$, $ArNH_2$, $NH_3$, $I^-$, $Br^-$, $Cl^-$, $RCOO^-$, $SCN^-$, $ROH$, $RSH$, $NCO^-$, $CN^-$, $NO_3^-$, $ClO_4^-$, $H_2O$.

22. The method of claim 1, wherein the composition is applied to hair by pre-impregnating the hair using a nucleophilic agent other than water.

23. The method of claim 1, wherein the nucleophilic agent is in pure form, a solution, in the form of an emulsion, or encapsulated.

24. The method of claim 1, wherein application of the composition containing the at least, one monomer is followed by rinsing.

25. The method of claim 1, wherein the hair is moistened with an aqueous solution whose pH has been adjusted with the aid of a base, an acid, or an acid/base mixture.

26. The method of claim 1, wherein the nucleophilic agent is water.

27. The method of claim 26, wherein the water is provided by moistening the hair before application of the composition.

* * * * *

UNITED STATES PATENT AND TRADEMARK OFFICE
CERTIFICATE OF CORRECTION

PATENT NO. : 7,357,921 B2 Page 1 of 1
APPLICATION NO. : 10/323991
DATED : April 15, 2008
INVENTOR(S) : Franck Giroud It is certified that error appears in the above-identified patent and that said Letters Patent is hereby corrected as shown below:

On the title page, item (30) Foreign Application Priority Data, insert
--December 18, 2001    (FR)    01 16402--.

In claim 6, column 7, line 57, insert space between "2-propoxyethyl" and "2-cyanoacrylate".

In claim 24, column 8, line 56, delete comma between "least" and "one".

Signed and Sealed this

Fifteenth Day of July, 2008

JON W. DUDAS
*Director of the United States Patent and Trademark Office*